(12) United States Patent
Langhorn et al.

(10) Patent No.: US 10,874,404 B2
(45) Date of Patent: Dec. 29, 2020

(54) CUSTOMIZED PATIENT-SPECIFIC SURGICAL INSTRUMENTS AND METHOD

(71) Applicant: DePuy Synthes Products, Inc., Raynham, MA (US)

(72) Inventors: Jason Langhorn, Warsaw, IN (US); Daniel D. Fritzinger, Warsaw, IN (US)

(73) Assignee: DePuy Synthes Products, Inc., Raynham, MA (US)

( * ) Notice: Subject to any disclaimer, the term of this patent is extended or adjusted under 35 U.S.C. 154(b) by 249 days.

(21) Appl. No.: 15/394,887

(22) Filed: Dec. 30, 2016

(65) Prior Publication Data

US 2018/0185097 A1 Jul. 5, 2018

(51) Int. Cl.
| | | |
|---|---|---|
| *A61B 17/15* | (2006.01) | |
| *A61B 34/10* | (2016.01) | |
| *A61B 17/17* | (2006.01) | |
| *C25D 5/54* | (2006.01) | |
| *C25D 5/02* | (2006.01) | |
| *A61B 17/00* | (2006.01) | |
| *A61B 17/56* | (2006.01) | |

(52) U.S. Cl.
CPC ............ *A61B 17/155* (2013.01); *A61B 17/15* (2013.01); *A61B 17/154* (2013.01); *A61B 17/17* (2013.01); *A61B 17/1703* (2013.01); *A61B 17/1746* (2013.01); *A61B 17/1764* (2013.01); *A61B 34/10* (2016.02); *C25D 5/02* (2013.01); *C25D 5/54* (2013.01); *A61B 17/157* (2013.01); *A61B 2017/00526* (2013.01); *A61B 2017/568* (2013.01); *A61B 2034/102* (2016.02); *A61B 2034/105* (2016.02); *A61B 2034/108* (2016.02)

(58) Field of Classification Search
CPC .......................... A61B 17/155; A61B 17/1764
See application file for complete search history.

(56) References Cited

U.S. PATENT DOCUMENTS

| | | | |
|---|---|---|---|
| 4,487,203 | A | 12/1984 | Androphy |
| 4,703,751 | A | 11/1987 | Pohl |
| 7,468,075 | B2 | 12/2008 | Lang et al. |
| 7,534,263 | B2 | 5/2009 | Burdulis, Jr. et al. |
| 7,615,054 | B1 | 11/2009 | Bonutti |

(Continued)

FOREIGN PATENT DOCUMENTS

| | | |
|---|---|---|
| AU | 2017200804 A1 | 2/2017 |
| CA | 2447694 A1 | 12/2002 |

(Continued)

OTHER PUBLICATIONS

Partial International Search Report, International Application No. PCT/US2017/063623, dated Feb. 7, 2018, 14 pages.

*Primary Examiner* — Amy R Sipp
(74) *Attorney, Agent, or Firm* — Barnes & Thornburg LLP (57) ABSTRACT

Customized patient-specific instruments configured to be selectively attached at predetermined locations of a patient's bone are disclosed. The customized patient-specific instruments may include a polymeric body including a bone-facing surface having a customized patient-specific negative contour shaped to match and receive a corresponding positive contour of the patient's bone at the predetermined location. The customized patient-specific instruments also include a metallic coating that defines one or more cutting slots. A method of performing an orthopaedic surgical procedure is also disclosed.

4 Claims, 8 Drawing Sheets

(56) References Cited

U.S. PATENT DOCUMENTS

| | | | |
|---|---|---|---|
| 7,747,305 B2 | 6/2010 | Dean et al. | |
| 7,983,777 B2 | 7/2011 | Melton et al. | |
| 8,083,745 B2 | 12/2011 | Lang et al. | |
| 8,167,888 B2 | 5/2012 | Steffensmeier | |
| 8,234,097 B2 | 7/2012 | Steines et al. | |
| 8,257,360 B2 | 9/2012 | Richard et al. | |
| 8,377,066 B2 | 2/2013 | Katrana et al. | |
| 8,439,926 B2 | 5/2013 | Bojarski et al. | |
| 8,500,740 B2 | 8/2013 | Bojarski et al. | |
| 8,617,175 B2 | 12/2013 | Park et al. | |
| 8,623,026 B2 | 1/2014 | Wong et al. | |
| 8,916,248 B2 | 12/2014 | McCrea et al. | |
| 9,675,471 B2 | 6/2017 | Bojarski et al. | |
| 10,251,654 B2 | 4/2019 | Fritzinger | |
| 2002/0068979 A1 | 6/2002 | Brown et al. | |
| 2003/0045883 A1 | 3/2003 | Chow et al. | |
| 2003/0100907 A1 | 5/2003 | Rosa et al. | |
| 2006/0122617 A1 | 6/2006 | Lavallee et al. | |
| 2009/0024131 A1 | 1/2009 | Metzger et al. | |
| 2009/0087276 A1* | 4/2009 | Rose | A61B 17/1764 409/79 |
| 2009/0088753 A1 | 4/2009 | Aram et al. | |
| 2009/0131941 A1 | 5/2009 | Park et al. | |
| 2009/0222014 A1 | 9/2009 | Bojarski et al. | |
| 2010/0023015 A1 | 1/2010 | Park | |
| 2010/0185202 A1 | 7/2010 | Lester et al. | |
| 2010/0212138 A1 | 8/2010 | Carroll et al. | |
| 2010/0217270 A1 | 8/2010 | Polinski et al. | |
| 2011/0087332 A1 | 4/2011 | Bojarski et al. | |
| 2012/0041446 A1 | 2/2012 | Wong et al. | |
| 2012/0109135 A1* | 5/2012 | Bailey | A61B 17/17 606/87 |
| 2012/0123422 A1 | 5/2012 | Agnihotri et al. | |
| 2012/0209394 A1 | 8/2012 | Bojarski et al. | |
| 2012/0277751 A1 | 11/2012 | Catanzarite et al. | |
| 2012/0303131 A1* | 11/2012 | Chana | A61B 17/154 623/20.32 |
| 2012/0323246 A1 | 12/2012 | Catanzarite et al. | |
| 2013/0296874 A1 | 11/2013 | Chao | |
| 2013/0317510 A1 | 11/2013 | Couture et al. | |
| 2014/0094814 A1 | 4/2014 | Hughes et al. | |
| 2014/0257306 A1 | 9/2014 | Edwards et al. | |
| 2015/0088143 A1 | 3/2015 | Lipman et al. | |
| 2015/0157341 A1 | 6/2015 | Catanzarite et al. | |
| 2017/0027587 A1 | 2/2017 | Fraone et al. | |
| 2018/0177512 A1 | 6/2018 | Hogan et al. | |
| 2019/0223886 A1 | 7/2019 | Fritzinger | |
| 2019/0223887 A1 | 7/2019 | Fritzinger et al. | |
| 2019/0223891 A1 | 7/2019 | Fritzinger | |

FOREIGN PATENT DOCUMENTS

| | | | |
|---|---|---|---|
| CA | 2696584 A1 | 2/2009 | |
| CA | 2753485 A1 | 9/2010 | |
| CA | 2795724 A1 | 11/2011 | |
| EP | 2649951 A2 | 10/2013 | |
| EP | 3096693 A1 | 11/2016 | |
| FR | 2918554 A1 | 1/2009 | |
| WO | 9414366 A2 | 7/1994 | |
| WO | WO-9414366 A2 * | 7/1994 | A61B 17/15 |
| WO | 2005084558 A1 | 9/2005 | |
| WO | 2008157412 A2 | 12/2008 | |
| WO | 2009111639 A1 | 9/2009 | |
| WO | 2010121147 A1 | 10/2010 | |
| WO | 2011106409 A1 | 9/2011 | |
| WO | 2011106430 A1 | 9/2011 | |
| WO | 2012024317 A2 | 2/2012 | |
| WO | 2015048319 A1 | 4/2015 | |
| WO | 2015121400 A1 | 8/2015 | |
| WO | 2015185865 A1 | 12/2015 | |
| WO | 2017007820 A1 | 1/2017 | |

* cited by examiner

CUSTOMIZED PATIENT-SPECIFIC SURGICAL INSTRUMENTS AND METHOD

TECHNICAL FIELD

The present disclosure relates generally to customized orthopaedic surgical instruments, and in particular to metal-plated surgical instruments.

BACKGROUND

Joint arthroplasty is a well-known surgical procedure by which a diseased and/or damaged natural joint is replaced by a prosthetic joint. For example, in a total knee arthroplasty surgical procedure, a patient's natural knee joint is partially or totally replaced by a prosthetic knee joint or knee prosthesis. A typical knee prosthesis includes a tibial tray, a femoral component, and a polymer insert or bearing positioned between the tibial tray and the femoral component. In a hip replacement surgical procedure, a patient's natural acetabulum is replaced by a prosthetic cup and a patient's natural femoral head is partially or totally replaced by a prosthetic stem and femoral ball.

To facilitate the replacement of the natural joint with a prosthesis, orthopaedic surgeons use a variety of orthopaedic surgical instruments such as, for example, cutting blocks, drill guides, milling guides, and other surgical instruments. Typically, the orthopaedic surgical instruments are generic with respect to the patient such that the same orthopaedic surgical instrument may be used on a number of different patients during similar orthopaedic surgical procedures.

The orthopaedic surgical instruments may also be customized to a specific patient. Such "customized patient-specific orthopaedic surgical instruments" are surgical tools for use by a surgeon in performing an orthopaedic surgical procedure that is intended, and configured, for use on a particular patient. It should be appreciated that these instruments are distinct from standard, non-patient specific orthopaedic surgical instruments that are intended for use on a variety of different patients. These customized patient-specific orthopaedic surgical instruments are distinct from orthopaedic prostheses, whether patient-specific or generic, which are surgically implanted in the body of the patient. Rather, customized patient-specific orthopaedic surgical instruments are used by an orthopaedic surgeon to assist in the implantation of orthopaedic prostheses.

SUMMARY

According to one aspect of the disclosure, a customized patient-specific instrument is disclosed. The customized patient-specific instrument is configured to be selectively attached at predetermined locations of a patient's bone are disclosed. The customized patient-specific instrument comprises a polymeric body including a bone-facing surface having a customized patient-specific negative contour shaped to match and receive a corresponding positive contour of the patient's bone at the predetermined location. The customized patient-specific instrument also includes a metallic coating on the polymeric body that defines a cutting slot. The metallic coating may also be applied to other parts of the polymeric body to strengthen the customized patient-specific instrument. A method of performing an orthopaedic surgical procedure is also disclosed.

According to another aspect of the disclosure, an orthopaedic surgical instrument comprising a customized patient-specific instrument configured to be selectively attached at a predetermined location of a patient's bone is disclosed. The customized patient-specific instrument comprises a polymeric body including a bone-facing surface having a customized patient-specific negative contour shaped to match and receive a corresponding positive contour of the patient's bone at the predetermined location, an outer surface positioned opposite the bone-facing surface, and an inner wall extending between a first opening defined in the bone-facing surface and a second opening defined in the outer surface. A metallic coating is positioned on a first section of the inner wall extending inwardly from the first opening and a second section of the inner wall extending inwardly from the second opening. The inner wall includes a central section positioned between the first section and the second section that is offset from the first section and the second section such that a distance greater than 0 mm is defined between the central section and each of the first section and the second section.

In some embodiments, the metallic coating on the first section of the inner wall may define a first planar cutting guide surface and the metallic coating on the second section of the inner wall defines a second planar cutting guide surface.

In some embodiments, the inner wall may be a first inner wall, and the polymeric body may include a second inner wall positioned opposite the first inner wall extending between the first opening and the second opening. The metallic coating may be formed on a first section of the second inner wall extending inwardly from the first opening and a second section of the second inner wall extending inwardly from the second opening. The first sections of the first inner wall and the second inner wall may cooperate to define a first cutting slot of a cutting guide sized to receive a cutting tool and the second sections of the first inner wall and the second inner wall may cooperate to define a second cutting slot of the cutting guide.

Additionally, in some embodiments, at least one of the first cutting slot and the second cutting slot may have a first thickness, and the second inner wall may include a central section positioned opposite the central section of the first inner wall. The central sections of the first inner wall and the second inner wall may cooperate to define a passageway having a second thickness greater than the first thickness such that the central sections are spaced apart from the cutting tool when the cutting tool is positioned in the cutting guide.

In some embodiments, the inner wall may include a first sloped surface extending between the first section and the central section and a second slope surface extending between the second section and the central section. Additionally, in some embodiments, the central section of the inner wall may be substantially devoid of the metallic coating.

In some embodiments, the metallic coating on the first section of the inner wall may define a first cylindrical passageway, and the metallic coating on the second section of the inner wall may define a second cylindrical passageway. The first cylindrical passageway and the second cylindrical passageway may define a cutting guide sized to receive a cutting tool.

Additionally, in some embodiments, the first cylindrical passageway may have a first diameter, the second cylindrical passageway may have a second diameter, and the central section may define a cylindrical passageway having a third diameter that is greater than each of the first diameter and the second diameter such that the central section is spaced apart from a cutting tool when the cutting tool is positioned in the cutting guide.

In some embodiments, the polymeric body may include a bore extending from an inner opening defined in the inner wall of the body to an outer opening defined in the outer surface. The bore may extende along a second axis extending orthogonal to the axis of the inner wall as it extends from the first opening defined in the bone-facing surface and a second opening defined in the outer surface.

According to another aspect, a customized patient-specific instrument configured to be selectively attached at a predetermined location of a patient's bone comprises a polymeric body including a bone-facing surface including a customized patient-specific negative contour shaped to match and receive a corresponding positive contour of the patient's bone at the predetermined location, a non-bone facing outer surface, an inner wall defining a passageway extending through the polymeric body along a first axis, and a bore extending from an inner opening defined in the inner wall to an outer opening defined in the outer surface. The bore extends along a second axis extending orthogonal to the first axis. The customized patient-specific instrument also includes a metallic coating positioned on the inner wall to define a cutting guide sized and shaped to receive a cutting tool.

In some embodiments, the metallic coating may line a section of the bore. In some embodiments, the bore may include a first section positioned on one side of the passageway and a second section positioned on the opposite side of the passageway. The first section of the bore may extend to the outer opening defined in the outer surface, and the second section may extend to a second outer opening defined in a second outer surface. Additionally, in some embodiments, the metallic coating may terminate at the outer edges of the polymeric body surrounding the passageway.

In some embodiments, the cutting guide may be a cutting slot sized and shaped to receive a cutting saw blade. In some embodiments, the cutting guide may be a cylindrical passageway that is sized and shaped to receive a cutting drill.

According to another aspect, a method of fabricating an orthopaedic surgical instrument is disclosed. The method comprises forming a polymeric body including at least one surface having a customized patient-specific negative contour shaped to match and receive a corresponding positive contour of a patient's bone at a predetermined location of the patient's bone, and advancing an electrolyte solution containing metallic salts into a passageway of the polymeric body to coat a section of the polymeric body. The method further comprises forming the metallic coating from the metallic salts on the section of the polymeric body that defines a cutting guide sized and shaped to receive a cutting tool.

In some embodiments, advancing the electrolyte solution containing metallic salts may comprise advancing the electrolyte solution containing metallic salts into the bore extending orthogonal to the passageway from an outer opening of the polymeric body to an inner opening, and advancing the electrolyte solution containing metallic salts into the inner opening into the passageway.

In some embodiments, forming the polymeric body may include forming the outer opening in a non-bone facing surface. Additionally, in some embodiments, forming the polymeric body may include forming a first opening in the at least one surface and a second opening in a non-bone facing surface, and forming an inner wall that defines the passageway. The inner wall may have a first section extending inwardly from the first opening, a second section extending inwardly from the second opening, and a central section positioned between the first section and the second section. The central section may be offset from the first section and the second section such that a distance greater than 0 mm is defined between the central section and each of the first section and second section. Further, advancing the electrolyte solution containing metallic salts may comprise advancing the metallic material along the first section of the inner wall to form the metallic coating on the first section, and advancing the salt solution along the second section of the inner wall to form the metallic coating on the second section.

In some embodiments, the central section of the inner wall is substantially devoid of the metallic coating.

BRIEF DESCRIPTION OF THE DRAWINGS

The detailed description particularly refers to the following figures, in which.

DETAILED DESCRIPTION OF THE DRAWINGS

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout the specification in reference to the orthopaedic implants and surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise.

Figure 1:
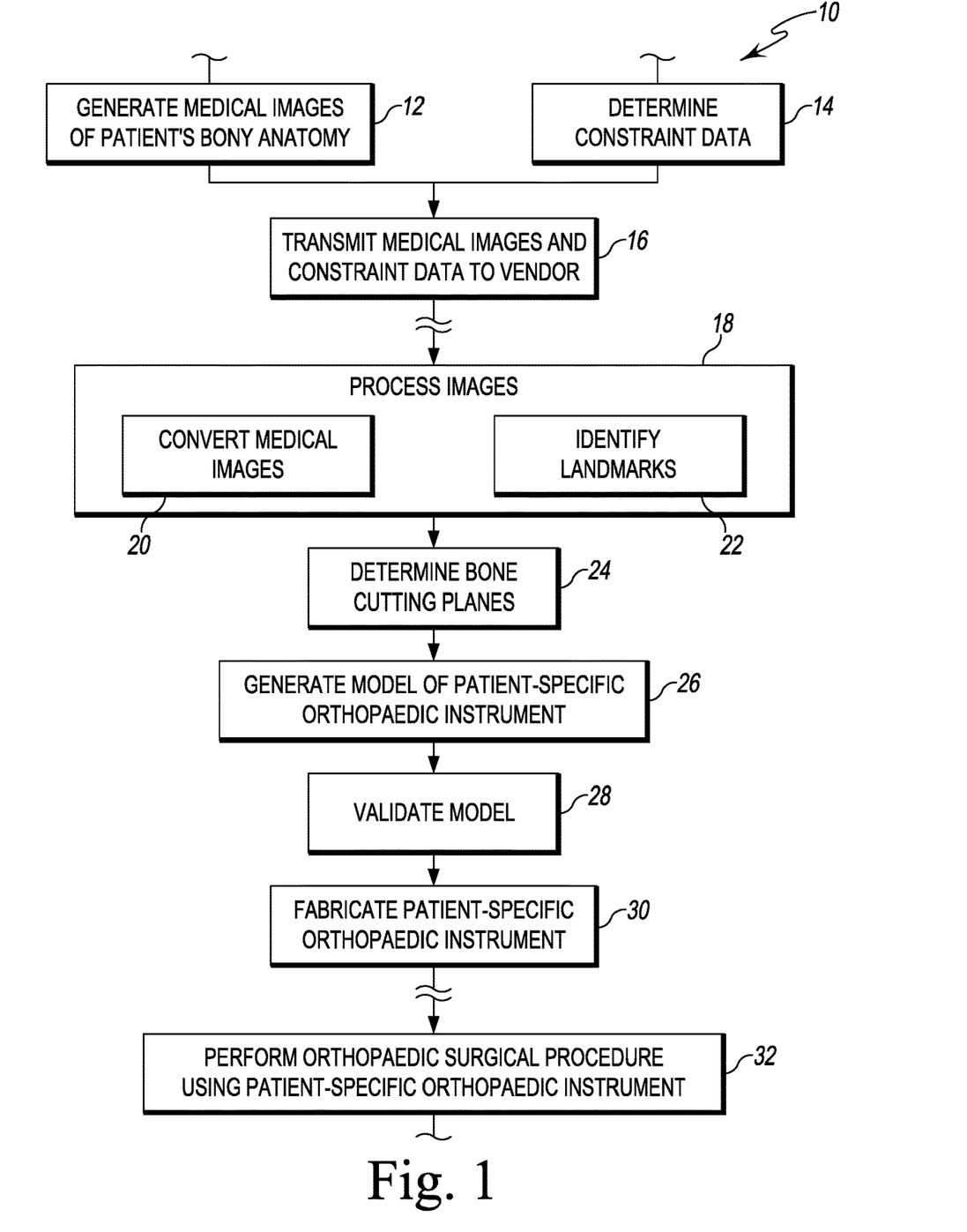
FIG. 1 is a simplified flow diagram of an algorithm for designing and fabricating a customized patient-specific orthopaedic surgical instrument.

Referring to FIG. 1, an algorithm 10 for fabricating a customized patient-specific orthopaedic surgical instrument is illustrated. What is meant herein by the term "customized patient-specific orthopaedic surgical instrument" is a surgical tool for use by a surgeon in performing an orthopaedic surgical procedure that is intended, and configured, for use on a particular patient. As such, it should be appreciated that, as used herein, the term "customized patient-specific orthopaedic surgical instrument" is distinct from standard, non-patient specific orthopaedic surgical instruments (i.e., "patient-universal instruments" such as patient-universal cutting blocks) that are intended for use on a variety of different patients and were not fabricated or customized to any particular patient. Additionally, it should be appreciated that, as used herein, the term "customized patient-specific orthopaedic surgical instrument" is distinct from orthopaedic prostheses or implants, whether patient-specific or generic, which are surgically implanted in the body of the patient. Rather, an orthopaedic surgeon uses customized patient-specific orthopaedic surgical instruments to assist in the implantation of orthopaedic prostheses. Examples of "customized patient-specific orthopaedic surgical instruments" include customized patient-specific drill/pin guides, customized patient-specific tibial cutting guide blocks, customized patient-specific femoral cutting guide blocks, and customized patient-specific alignment guides.

As shown in FIG. 1, the method 10 includes process steps 12 and 14, in which an orthopaedic surgeon performs pre-operative planning of the orthopaedic surgical procedure to be performed on a patient. The process steps 12 and 14 may be performed in any order or contemporaneously with each other. In process step 12, a number of medical images of the relevant portions of a patient's bone are generated. For example, for a knee replacement surgery, the medical images may include images of the distal end of a patient's femur and the proximal end of a patient's tibia. For a hip replacement surgery, the medical images may include images of the patient's acetabulum and surrounding bony anatomy, as well as images of the proximal end of the patient's femur. To do so, the orthopaedic surgeon or other healthcare provider may operate an imaging system to generate the medical images. The medical images may be embodied as any number and type of medical images capable of being used to generate a three-dimensional rendered model of the patient's acetabulum and surrounding bony anatomy. For example, the medical images may be embodied as any number of computed tomography (CT) images, magnetic resonance imaging (MRI) images, or other three-dimensional medical images. Additionally, or alternatively, as discussed in more detail below in regard to process step 18, the medical images may be embodied as a number of X-ray images or other two-dimensional images from which a three-dimensional rendered model of the relevant area of the patient's bone.

In process step 14, the orthopaedic surgeon may determine any additional pre-operative constraint data. The constraint data may be based on the orthopaedic surgeon's preferences, preferences of the patient, anatomical aspects of the patient, guidelines established by the healthcare facility, or the like. For example, in a knee replacement surgery, the constraint data may include the type and size of the knee prosthesis, the amount of distal and posterior resections to be performed on the patient's femur and so forth. In a hip replacement surgery, the constraint data may include the orthopaedic surgeon's preference for the amount of inclination and version for an acetabular prosthesis, the amount of the bone to ream, the size range of the orthopaedic implant, and/or the like. In some embodiments, the orthopaedic surgeon's preferences are saved as a surgeon's profile, which may be used as a default constraint values for further surgical plans.

In process step 16, the medical images and the constraint data, if any, may be transmitted or otherwise provided to an orthopaedic surgical instrument vendor or manufacturer. The medical images and the constraint data may be transmitted to the vendor via electronic means such as a network or the like. After the vendor has received the medical images and the constraint data, the vendor processes the images in step 18. The orthopaedic surgical instrument vendor or manufacturer process the medical images to facilitate the determination of the proper planes of inclination and version, implant sizing, and fabrication of the customized patient-specific orthopaedic surgical instrument as discussed in more detail below.

In process step 20, the vendor may convert or otherwise generate three-dimensional images from the medical images. For example, in embodiments wherein the medical images are embodied as a number of two-dimensional images, the vendor may use a suitable computer algorithm to generate one or more three-dimensional images form the number of two-dimensional images. Additionally, in some embodiments, the medical images may be generated based on an established standard such as the Digital Imaging and Communications in Medicine (DICOM) standard. In such embodiments, an edge-detection, thresholding, watershed, or shape-matching algorithm may be used to convert or reconstruct images to a format acceptable in a computer aided design application or other image processing application.

In process step 22, the vendor may process the medical images, and/or the converted/reconstructed images from process step 20, to determine a number of aspects related to the bony anatomy of the patient such as the anatomical axis of the patient's bones, the mechanical axis of the patient's bone, other axes and various landmarks, and/or other aspects of the patient's bony anatomy. To do so, the vendor may use any suitable algorithm to process the images.

In process step 24, the desired cutting planes for implantation of the orthopaedic prosthesis are determined. The planned cutting planes may be determined based on the type, size, and position of the orthopaedic prosthesis to be used during the orthopaedic surgical procedure; the process images, such as specific landmarks identified in the images; and the constraint data supplied by the orthopaedic surgeon in process steps 14 and 16. The type and/or size of the orthopaedic prosthesis may be determined based on the patient's anatomy and the constraint data. For example, the constraint data may dictate the type, make, model, size, or other characteristic of the orthopaedic prosthesis. The selection of the orthopaedic prosthesis may also be modified based on the medical images such that an orthopaedic prosthesis that is usable with the bone of the patient and that matches the constraint data or preferences of the orthopaedic surgeon is selected.

In addition to the type and size of the orthopaedic prosthesis, the planned location and position of the orthopaedic prosthesis relative to the patient's bony anatomy is determined. To do so, a digital template of the orthopaedic prosthesis may be overlaid onto one or more of the processed medical images. The vendor may use any suitable algorithm to determine a recommended location and orientation of the orthopaedic prosthesis (i.e., the digital template) with respect to the patient's bone based on the processed medical images (e.g., landmarks of the patient's acetabulum defined in the images) and/or the constraint data.

Additionally, any one or more other aspects of the patient's bony anatomy may be used to determine the proper positioning of the digital template.

In process step 26, a model of the customized patient-specific orthopaedic surgical instrument is generated. In some embodiments, the model is embodied as a three-dimensional rendering of the customized patient-specific orthopaedic surgical instrument. In other embodiments, the model may be embodied as a mock-up or fast prototype of the customized patient-specific orthopaedic surgical instrument. The patient-specific orthopaedic surgical instrument to be modeled and fabricated may be determined based on the orthopaedic surgical procedure to be performed, the constraint data, and/or the type of orthopaedic prosthesis to be implanted in the patient.

The particular shape of the customized patient-specific an orthopaedic surgical instrument is determined based on the planned location and implantation angles of the orthopaedic prosthesis relative to the patient's bone. Additionally, the planned location of the orthopaedic surgical instrument may be based on the identified landmarks of the patient's bone identified in process step 22.

In some embodiments, the particular shape or configuration of the customized patient-specific orthopaedic surgical instrument may be determined based on the planned location of the instrument relative to the patient's bony anatomy. That is, the customized patient-specific orthopaedic surgical instrument may include a bone-contacting surface having a negative contour that matches the corresponding contour of a portion of the bony anatomy of the patient such that the orthopaedic surgical instrument may be coupled to the bony anatomy of the patient in a unique location, which corresponds to the pre-planned location for the instrument. Such negative contours may include a unique set of ridges and depressions shaped to match a corresponding set of ridges and depressions on the patient' bone. When the orthopaedic surgical instrument is coupled to the patient's bony anatomy in the unique location, one or more guides (e.g., cutting or drilling guide) of the orthopaedic surgical instrument may be aligned to the inclination and version planes, as discussed above.

After the model of the customized patient-specific orthopaedic surgical instrument has been generated in process step 26, the model is validated in process step 28. The model may be validated by, for example, analyzing the rendered model while coupled to the three-dimensional model of the patient's anatomy to verify the correlation of cutting guides, reaming guides, inclination and version planes, and/or the like. Additionally, the model may be validated by transmitting or otherwise providing the model generated in step 26 to the orthopaedic surgeon for review.

After the model has been validated in process step 28, the customized patient-specific orthopaedic surgical instrument is fabricated in process step 30. The customized patient-specific orthopaedic surgical instrument may be fabricated using any suitable fabrication device and method. Additionally, the customized patient-specific orthopaedic instrument may be formed from any suitable material such as a metallic material, a plastic material, or combination thereof depending on, for example, the intended use of the instrument.

In the illustrative embodiment, a polymeric body may be formed via injection molding technique and/or using a stereolithography technique. The polymeric body may include at least one surface having a customized patient-specific negative contour that is shaped to match and receive a corresponding positive contour of the patient's bone at a predetermined location of the patient's bone.

The polymeric body may then be positioned in a fixture in which electrolyte solutions containing metals salts may be advanced across the surfaces and along one or more passageways of the polymeric body to coat sections of the polymeric body. One commercially available technique for applying a metallic coating to a polymeric substrate is commercially available from Integran Technologies. One technique for applying a metallic coating to a polymeric substrate is described in U.S. Pat. No. 8,916,248, which is expressly incorporated herein by reference. The fabricated customized patient-specific orthopaedic instrument is subsequently shipped or otherwise provided to the orthopaedic surgeon.

The surgeon performs the orthopaedic surgical procedure in process step 32 using the customized patient-specific orthopaedic surgical instrument. As discussed above, because the orthopaedic surgeon does not need to determine the proper location of the orthopaedic surgical instrument intra-operatively, which typically requires some amount of estimation on part of the surgeon, the guesswork and/or intra-operative decision-making on part of the orthopaedic surgeon is reduced.

It should also be appreciated that variations in the bony of anatomy of the patient may require more than one customized patient-specific orthopaedic surgical instrument to be fabricated according to the method described herein. For example, the patient may require the implantation of two orthopaedic prostheses. As such, the surgeon may follow the method 10 of FIG. 1 to fabricate a different customized patient-specific orthopaedic surgical instrument for use in replacing each portion of the patient's bony anatomy. Each customized patient-specific orthopaedic surgical instrument defines a cutting plane or other relevant parameter relative to each bone that is different due to the variation in the bony anatomy.

Referring now to FIGS. 2-6, the customized patient-specific orthopaedic surgical instrument may be embodied as a femoral cutting block 100, which is configured to be coupled to a femur of a patient. The cutting block 100 includes a base 102 configured to be coupled to the anterior side of the femur. Two tabs 104, 106 extend orthogonally from the base 102 and are configured to wrap around the distal end of the femur. Each of the tabs 104, 106 includes an inwardly curving lip 108, 110, respectively, that references the posterior condyles of the femur. The femoral cutting block 100 includes a bone-contacting or bone-facing surface 112 defined on the inside of the base 102, the tabs 104, 106, and the lips 108, 110. The bone-contacting surface 112 includes one or more negative contours 114 configured to receive a portion of the patient's bone having a corresponding contour. Each contour 114 has a unique set of ridges 116 and depression 118 that are shaped to engage a corresponding unique set of depressions and ridges of the patient's bone. As described above, the negative contour 114 of the bone-contacting surface 112 allows the positioning of the cutting block 100 on the patient's bone in a unique pre-determined location and orientation.

In the illustrative embodiment, the base 102 and tabs 104, 106 are formed as a single, monolithic component from a polymeric material. The polymeric material may be plastic such as, for example, polyethylene or another biocompatible plastic. It should be appreciated that in other embodiments the base may be formed as a separate component from one or both of the tabs and may be later assembled to form the cutting block. In still other embodiments, one or more of the base and tabs may be formed from a metallic material such as stainless steel.

Figure 2:
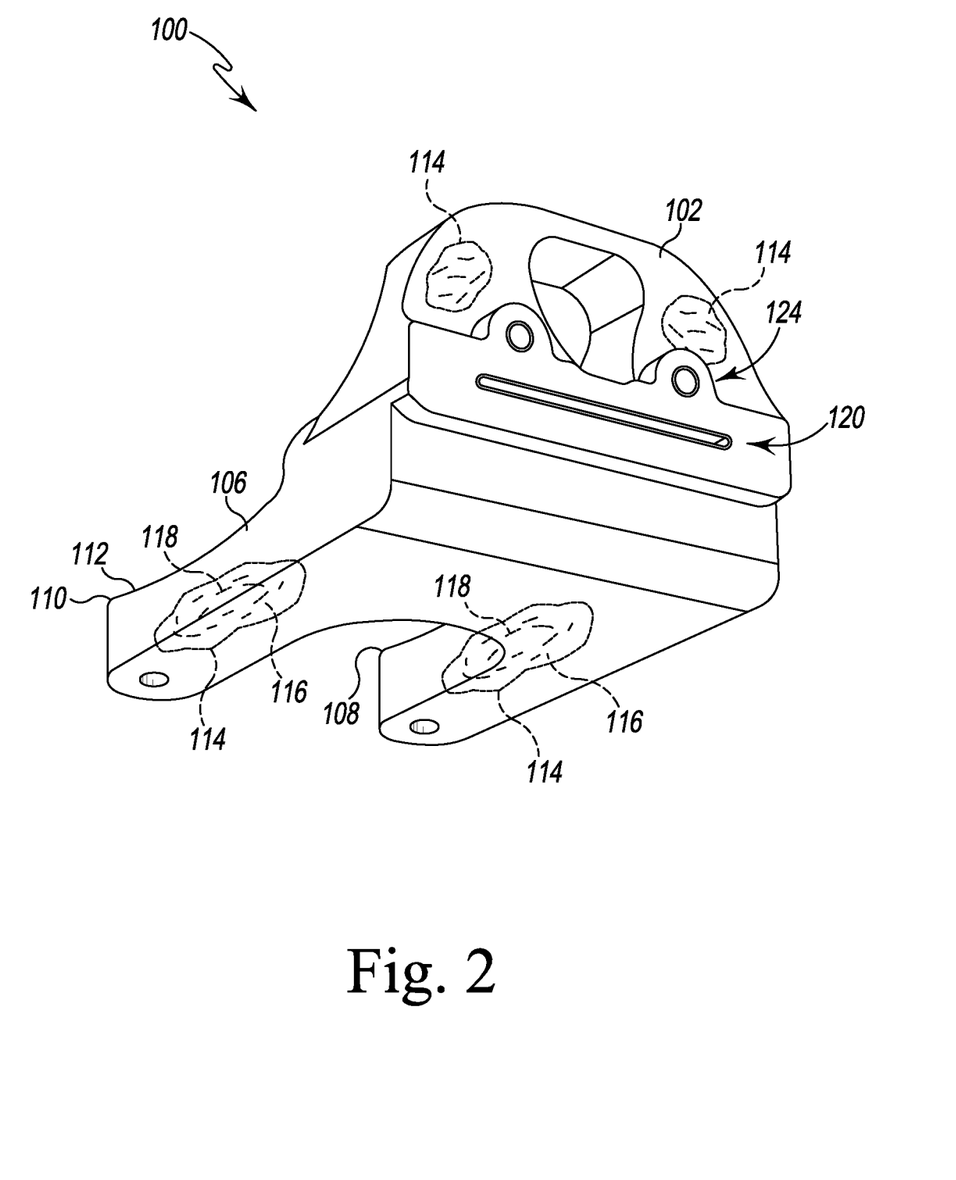
FIG. 2 is a perspective view of a customized patient specific orthopedic surgical instrument.
Figure 3:
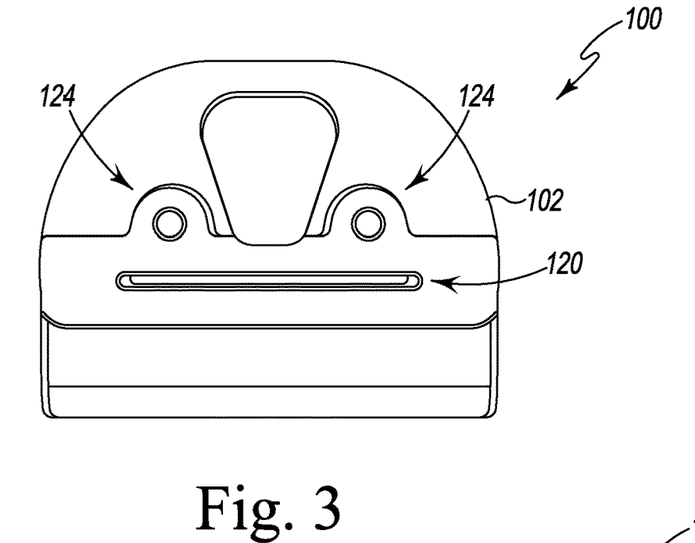
FIG. 3 is a front elevation view of the surgical instrument of FIG. 2.

As shown in FIG. 2, the cutting block 100 also includes a cutting guide 120 that extends through the base 102. As described in greater detail below, the cutting guide 120 is sized to receive a cutting blade 122 (see FIG. 5), which the surgeon may use to resect a portion of the patient's bone. A pair of anterior pin guides 124 are positioned above the cutting guide 120 in the illustrative embodiment. Each pin guide 124 is sized to receive a surgical drill 126 (see FIG. 6), which the surgeon may use to establish pinholes in the femur.

Figure 4:
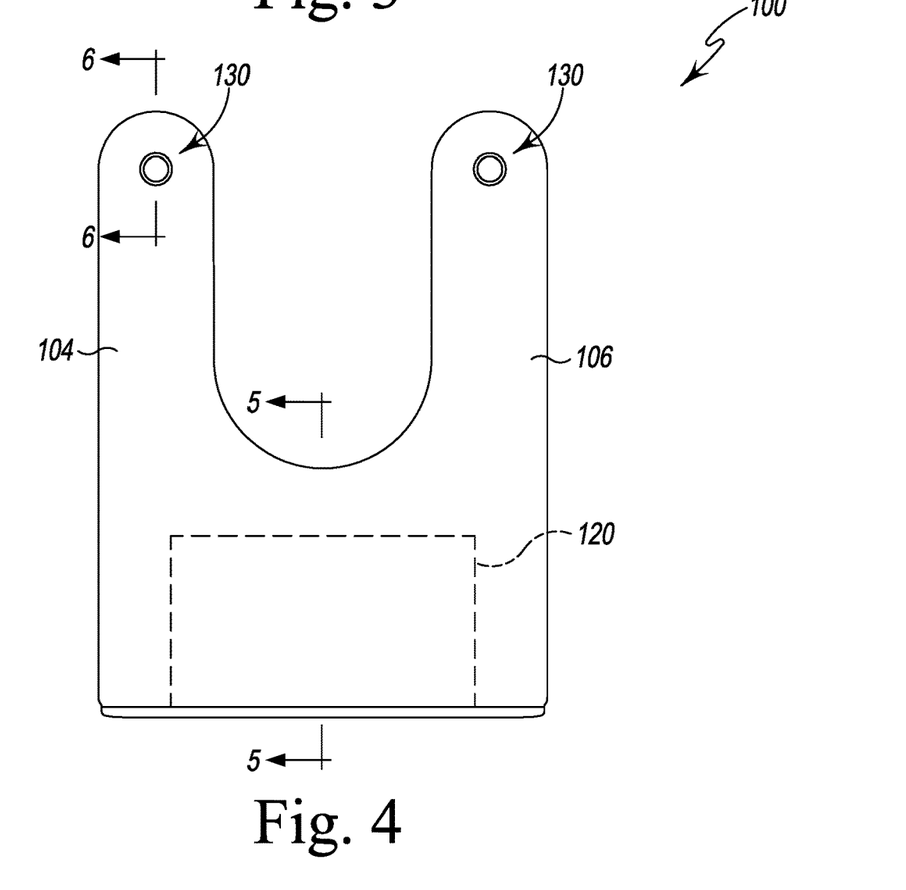
FIG. 4 is a top plan view of the surgical instrument of FIGS. 2-3.
Figure 6:
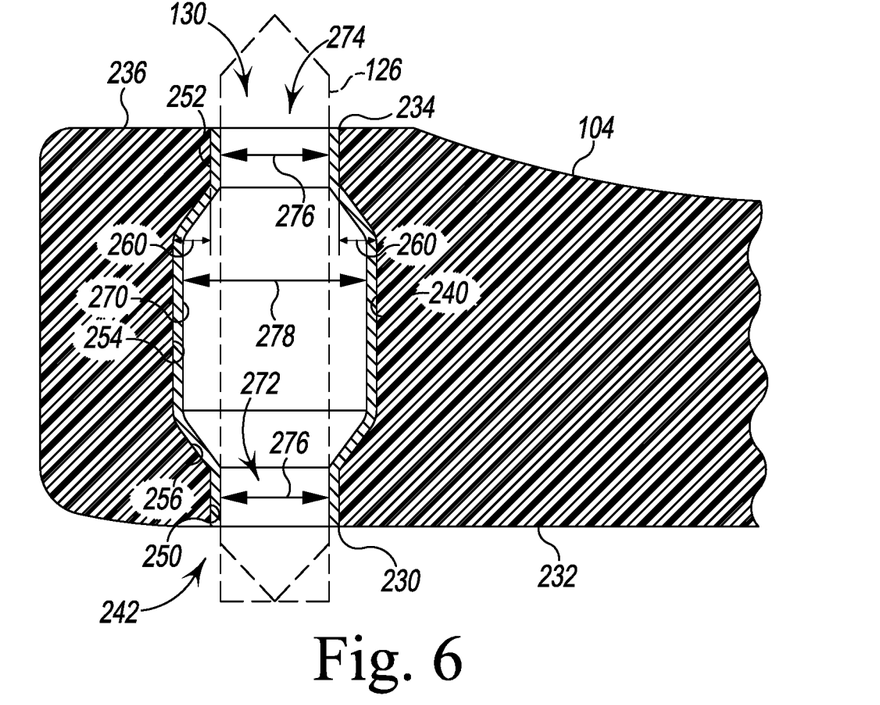
FIG. 6 is a partial cross-sectional elevation view taken along the line 6-6 in FIG. 4.

As shown in FIG. 4, the cutting block 100 includes a pair of distal pin guides 130 that are defined in the tabs 104, 106. Each pin guide 130 is sized to receive the surgical drill 126, which the surgeon may use to establish pinholes in the femur. It should be appreciated that in other embodiments, guide pins may not be used. That is, the cutting block may be coupled to the femur of the patient via pressure applied by the base and the tabs.

Figure 5:
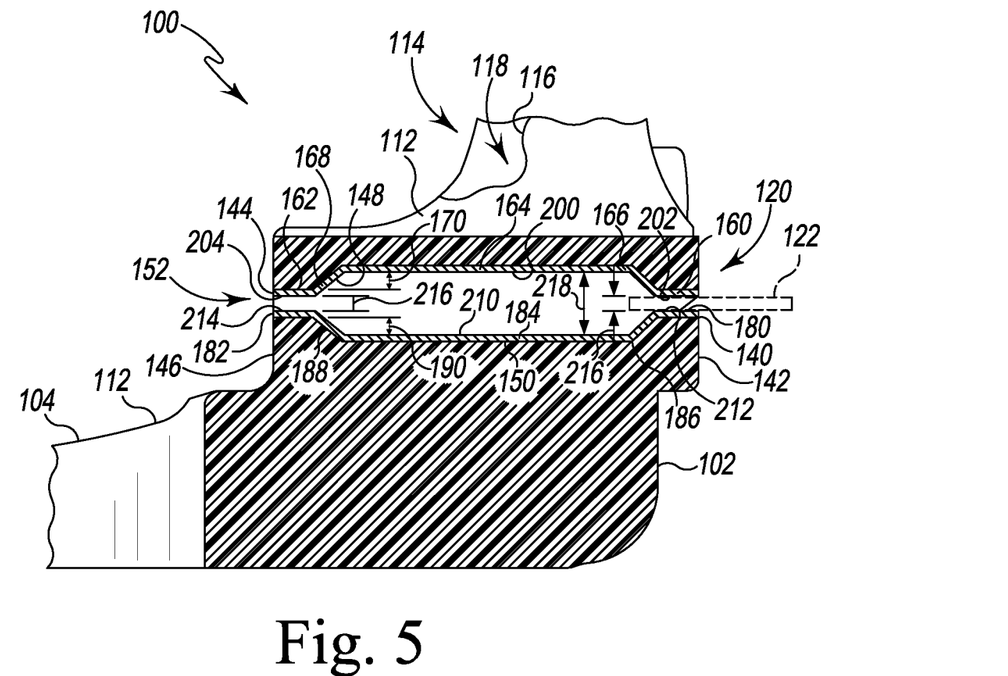
FIG. 5 is a partial cross-sectional elevation view taken along the line 5-5 in FIG. 4.

Referring now to FIG. 5, the cutting guide 120 of the cutting block 100 includes an opening 140 defined in an anterior surface 142 of the base 102. In the illustrative embodiment, the anterior surface 142 faces away from the patient's femur when the cutting block 100 is attached to the patient's bone. The cutting guide 120 includes another opening 144 defined in the opposite, posterior surface 146 of the base 102. An upper wall 148 and a lower wall 150 extend between the openings 140, 144. The walls 148, 150 cooperate with sidewalls (not shown) to define a passageway 152 extending through the base 102.

The upper wall 148 includes an anterior section 160 that extends inwardly from the opening 140, a posterior section 162 that extends inwardly from the opening 144, and a central section 164 positioned between the sections 160, 162. The upper wall 148 includes a sloped section 166 that connects the anterior section 160 to the central section 164. Another sloped section 168 connects the posterior section 162 to the central section 164. In other embodiments, the central section 164 may be connected to the sections 160, 162 by sections that extend substantially perpendicular the sections 160, 162, 164.

As shown in FIG. 5, the central section 164 is offset from the sections 160, 162 by a distance 170 that is greater than 0 mm. In the illustrative embodiment, the distance 170 is equal to about 2.0 millimeters. In other embodiments, the distance may be greater than or less than this amount. In the illustrative embodiment, the central section 164 is offset from the sections 160, 162 by the same amount. It should be appreciated that in other embodiments the central section may be sloped or irregular such that it is offset from the sections 160, 162 by different amounts.

The lower wall 150 has a configuration that substantially mirrors that of the upper wall 148. In the illustrative embodiment, the lower wall 150 has an anterior section 180 that extends inwardly from the opening 140, a posterior section 182 that extends inwardly from the opening 144, and a central section 184 positioned between the sections 180, 182. The lower wall 150 also includes a sloped section 186 that connects the anterior section 180 the central section 184, and another sloped section 188 that connects the posterior section 182 to the central section 184. As shown in FIG. 5, the central section 184 of the lower wall 150 is offset from sections 180, 182 by a distance 190 that is greater than 0 mm. In the illustrative embodiment, the distance 190 is equal to about 2.0 millimeters. In other embodiments, the distance may be greater than or less than this amount. In the illustrative embodiment, the distance 190 is equal to the distance 170. The central section 184 is offset from the sections 180, 182 by the same distance 190. It should be appreciated that in other embodiments the central section 184 may be sloped or irregular such that it is offset from the sections 180, 182 by different amounts. Due to the configuration of the upper wall 148 and the lower wall 150, the passageway 152 is narrower between the anterior sections 160, 180 and the posterior sections 162, 182 and wider between the central sections 164, 184.

As shown in FIG. 5, the upper wall 148 is covered by a metallic layer or coating 200. The coating 200 defines a substantially planar surface 202 adjacent to the opening 140 in the anterior surface 142 of the cutting block 100. The coating 200 also defines a substantially planar surface 204 adjacent to the opening 144 in the posterior surface 146 of the cutting block 100. In the illustrative embodiment, the coating 200 has substantially the same thickness along the entire upper wall 148. It should be appreciated that in other embodiments the thickness may vary, particularly in the central section 164. For example, in some embodiments, the central section 164 may be substantially devoid of any metallic material.

The lower wall 150 is also covered by a metallic layer or coating 210. In the illustrative embodiment, the configuration of the coating 210 substantially mirrors the configuration of the coating 200. Like the coating 200, the metallic coating 210 defines a substantially planar surface 212 adjacent to the opening 140 of the cutting block 100. The coating also defines a substantially planar surface 214 that is adjacent to the opening 144 of the cutting block 100. In the illustrative embodiment, the coating 210 has substantially the same thickness along the entire lower wall 158. It should be appreciated that in other embodiments the thickness may vary, particularly in the central section 184. For example, in some embodiments, the central section 184 may be substantially devoid of any metallic material.

As shown in FIG. 5, the planar surfaces 202, 212 cooperate to define an anterior cutting slot of the cutting guide 120. In that way, the planar surfaces 202, 202 define cutting guide surfaces of the cutting guide 120. Similarly, the planar surfaces 204, 214 cooperate to define a posterior cutting slot of the cutting guide 120 and hence define cutting guide surfaces as well. The anterior and posterior cutting slots each have a thickness 216 sized to receive and guide a cutting saw blade 122. In the illustrative embodiment, the central sections 164, 184 of the walls 148, 150 (including the coatings 200, 210 in the illustrative embodiment) define another thickness 218 that is greater than the thickness 216. In that way, the central sections 164, 184 are spaced apart from the cutting saw blade 122 as it extends through the cutting guide 120 and into contact with a patient's bone.

As described above, the cutting block 100 also includes a pair of distal pin guides 130 that are defined in the tabs 104, 106. Referring now to FIG. 6, each pin guide 130 includes an opening 230 defined in a distal surface 232 of its corresponding tab (tab 104 is shown in FIG. 6). In the illustrative embodiment, the distal surface 232 faces away from the patient's femur when the cutting block 100 is attached to the patient's bone. Each pin guide 130 also includes another opening 234 that is defined in the opposite, proximal surface 236 of its corresponding tab. In the illustrative embodiment, an inner wall 240 extends between the openings 230, 234 to define a passageway 242 extending through the tab.

The inner wall 240 includes a distal section 250 that extends inwardly from the opening 230, a proximal section 252 that extends inwardly from the opening 234, and a central section 254 positioned between the sections 250, 252. In the illustrative embodiment, each of the sections 250, 252, 254 as a substantially circular cross-section. A pair of frustoconical sections 256, 258 connect the sections 250, 252, respectively, to the central section 254. In other embodiments, the central section 254 may be connected to the sections 250, 252 by sections that extend substantially perpendicular the sections 250, 252, 254.

As shown in FIG. 6, the central section 254 is offset from the sections 250, 252 by a distance 260 that is greater than 0 mm. In the illustrative embodiment, the distance 260 is equal to about 2.0 millimeters. In other embodiments, the distance may be greater than or less than this amount. In the illustrative embodiment, the central section 254 is offset from the sections 250, 252 by the same amount. It should be appreciated that in other embodiments the central section may be sloped or irregular such that it is offset from the sections 250, 252 by different amounts.

As shown in FIG. 6, the inner wall 240 is covered by a metallic layer or coating 270. The coating 270 defines a distal cylindrical passageway 272 positioned adjacent to the distal opening 230. The coating 270 defines a proximal cylindrical passageway 274 positioned adjacent to the proximal opening 234. In the illustrative embodiment, the coating 270 has substantially the same thickness along the entire inner wall 240. It should be appreciated that in other embodiments the thickness may vary, particularly in the central section 254. For example, in some embodiments, the central section 254 may be substantially devoid of any metallic material.

The cylindrical passageway 272 defines a distal drill slot of the pin guide 130, while the cylindrical passageway 274 defines a proximal drill slot of the pen guide 130. The distal and proximal drill slots each have a diameter 276 that is sized to receive and guide a surgical drill 126. In the illustrative embodiment, the central section 254 (including the coating 270 in the illustrative embodiment) defines another diameter 278 that is greater than the diameter 276. In that way, the central section 254 is spaced apart from the surgical drill 126 as it extends through the pin guide 130 and into contact with a patient's bone. In the illustrative embodiment, the configurations of the anterior pin guides 124 mirrors that of the distal pin guides 130.

In one illustrative method, the block 100 may be manufactured by forming the base 102 and tabs 104, 106 as a single, monolithic component from a polymeric material. This single, monolithic component may then be immersed in an electrolyte solution containing metallic salts. The walls 148, 150, 240 may then be exposed to one or electrodes within the solution to form the metallic layers 200, 210, 270, respectively. It should be appreciated that in other embodiments other techniques may be used to form the metallic layers on the polymeric component.

It should also be appreciated that other surfaces of the polymeric component may be exposed to electrodes such that additional layers of metallic material are deposited on the polymeric component. In that way, the polymeric component may be stiffened or strengthen at various points by the metallic coating. Such strategic deposits of metallic coating may permit the structure of the polymeric component to be altered as necessary to provide better positioning of the block on the patient's bone. For example, the thickness of one of the tabs of the polymeric component may be reduced and the tab coated with a metallic layer so as to better fit on patient's bone.

Figure 7:
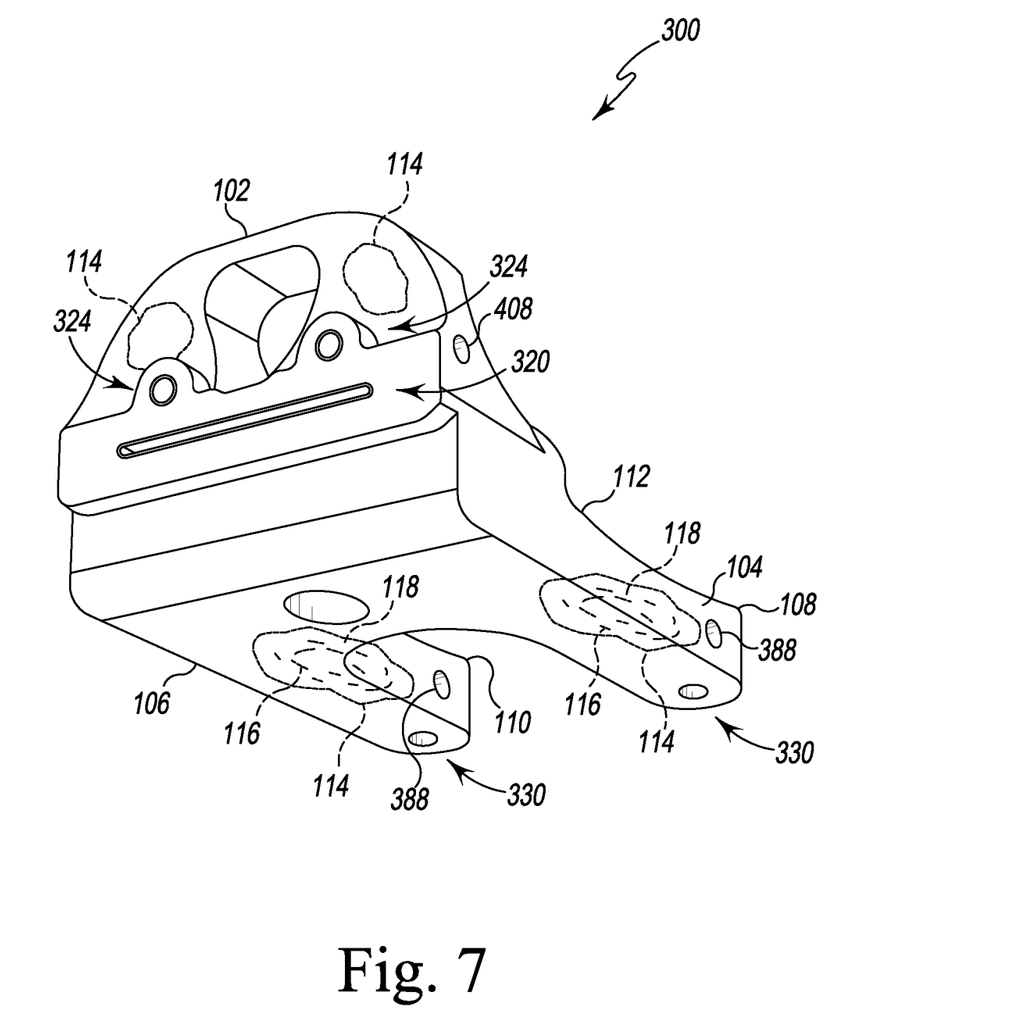
FIG. 7 is a perspective view of another embodiment of a customized patient specific orthopedic surgical instrument.

Referring now to FIGS. 7-12, another embodiment of a customized patient-specific surgical instrument (hereinafter femoral cutting block or cutting block 300) is shown. The cutting block 300 includes many features that are similar to those described in regard to the cutting block 100. Such features are identified with the same reference numbers in FIGS. 7-12 as those used in FIGS. 2-6. As shown in FIG. 7, the cutting block 300 includes a base 102 configured to be coupled to the anterior side of the femur. Two tabs 104, 106 extend orthogonally from the base 102 and are configured to wrap around the distal end of the femur, as described in more detail below. Each of the tabs 104, 106 includes an inwardly curving lip 108, 110, respectively, that references the posterior condyles of the femur. The femoral cutting block 100 includes a bone-contacting or bone-facing surface 112 defined on the inside of the base 102, the tabs 104, 106, and the lips 108, 110. The bone-contacting surface 112 includes one or more negative contours 114 configured to receive a portion of the patient's bone having a corresponding contour. Each contour 114 has a unique set of depressions 118 and ridges 116 that are shaped to engage a corresponding unique set of ridges and depressions of the patient's bone. As described above, the negative contour 114 of the bone-contacting surface 112 allows the positioning of the cutting block 100 on the patient's bone in a unique pre-determined location and orientation.

Figure 8:
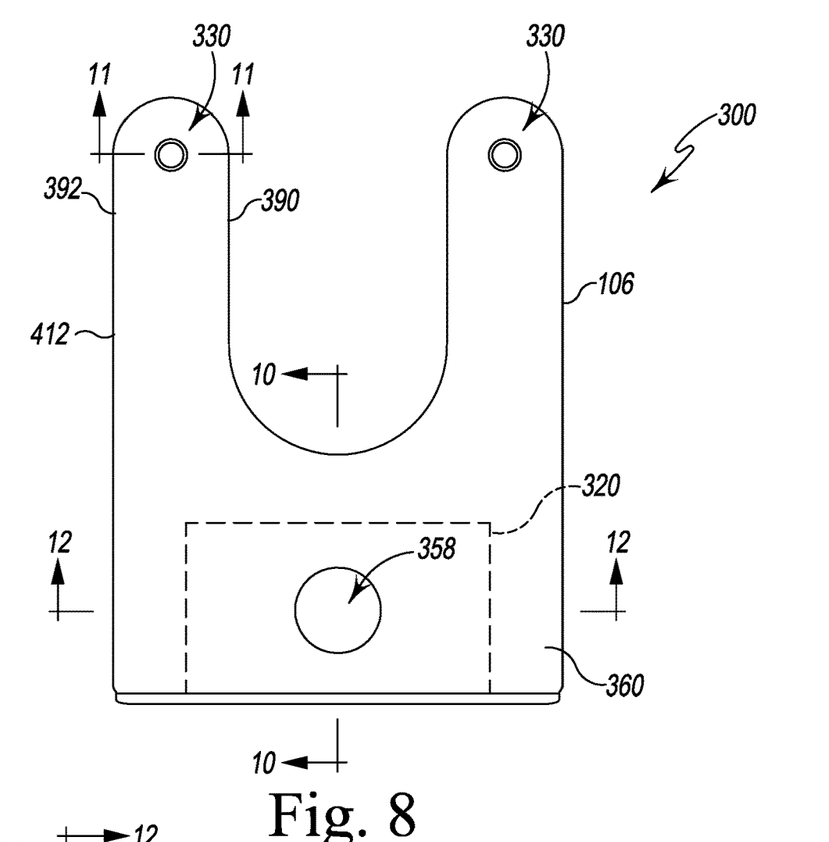
FIG. 8 is a front elevation view of the surgical instrument of FIG. 7.

As shown in FIG. 7, the cutting block 300 also includes a cutting guide 320 that extends through the base 102 and is sized to receive a cutting blade 122, which the surgeon may use to resect a portion of the patient's bone. A pair of anterior pin guides 324 are positioned above the cutting guide 320 in the illustrative embodiment. Each pin guide 324 is sized to receive a surgical drill 126, which the surgeon may use to establish pinholes in the femur. The cutting block 300 includes a pair of distal pin guides 330 that are defined in the tabs 104, 106, as shown in FIG. 8. Each pin guide 330 is sized to receive the surgical drill 126, which the surgeon may use to establish pinholes in the femur. It should be appreciated that in other embodiments, guide pins may not be used. That is, the cutting block may be coupled to the femur of the patient via pressure applied by the base and the tabs.

Figure 10:
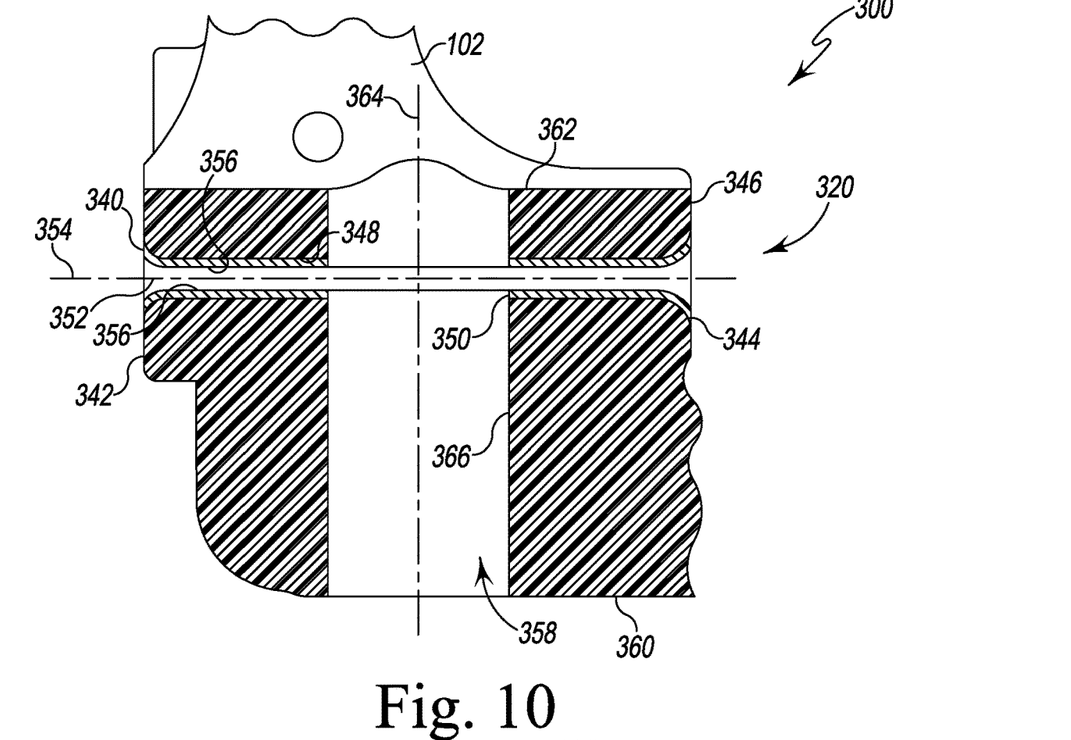
FIG. 10 is a partial cross-sectional elevation view taken along the line 10-10 in FIG. 8.

Referring now to FIG. 10, the cutting guide 320 of the cutting block 300 includes an opening 340 defined in an anterior surface 342 of the base 102. In the illustrative embodiment, the anterior surface 342 faces away from the patient's femur when the cutting block 300 is attached to the patient's bone. The cutting guide 320 includes another opening 344 defined in the opposite, posterior surface 346 of the base 102. An upper wall 348 and lower wall 350 extend between the openings 340, 344. The walls 348, 350 cooperate with sidewalls (not shown) to define a passageway 352 extending through the base 102. As shown in FIG. 10, the passageway 352 extends along an axis 354 that passes through the openings 340, 344. A metallic layer or coating 356 covers the walls 348, 350.

As shown in FIGS. 8 and 10, the base 102 includes a bore 358 that extends through a distal surface 360 and opposite proximal surface 362 of the base 102. In the illustrative embodiment, the bore 358 passes through the passageway 352 and extends along an axis 364 extending perpendicular to the axis 354 of the passageway 352. The bore 358 is defined by a cylindrical wall 366 extending between the surfaces 360, 362. In the illustrative embodiment, the wall 366 is substantially devoid of metallic coating. It should be appreciated that in other embodiments the bore 358 may not extend through both the distal and proximal surfaces 360, 362. It should also be appreciated that in some embodiments the bore may extend non-orthogonally to the passageway.

Figure 11:
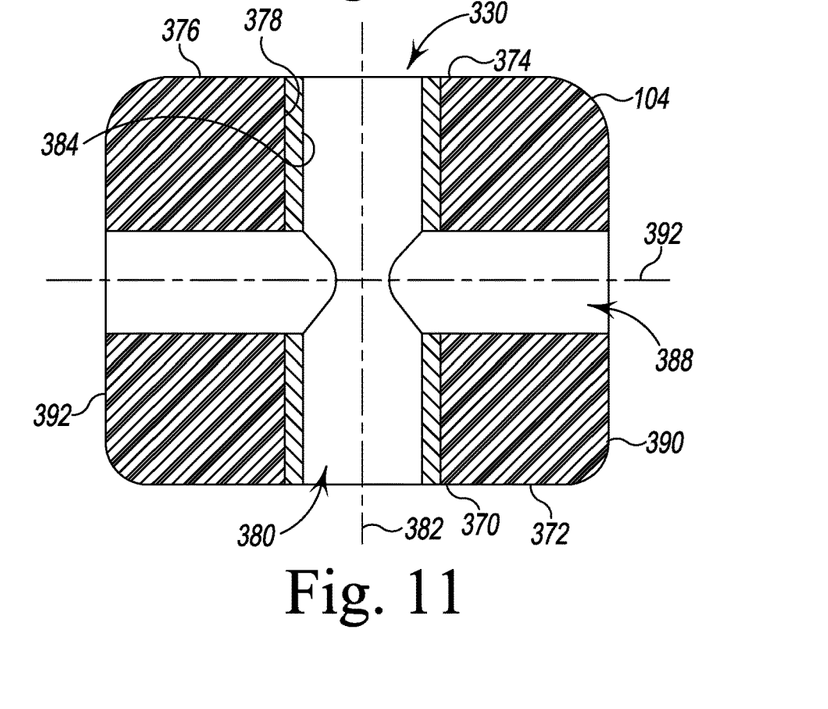
FIG. 11 is a partial cross-sectional elevation view taken along the line 11-11 in FIG. 8.

Referring now to FIG. 11, each pin guide 330 of the cutting block 300 includes an opening 370 defined in a distal surface 372 of one of the tabs (104 in FIG. 11). In the illustrative embodiment, the distal surface 372 faces away from the patient's femur when the cutting block 300 is attached to the patient's bone. The pin guide 330 includes another opening 374 defined in the opposite, posterior surface 376 of the tab. A cylindrical inner wall 378 extends between the openings 372, 374 to define a passageway 380 extending through the tab. As shown in FIG. 11, the passageway 380 extends along an axis 382 that passes through the openings 370, 374. A metallic layer or coating 384 covers the inner wall 378.

Figure 9:
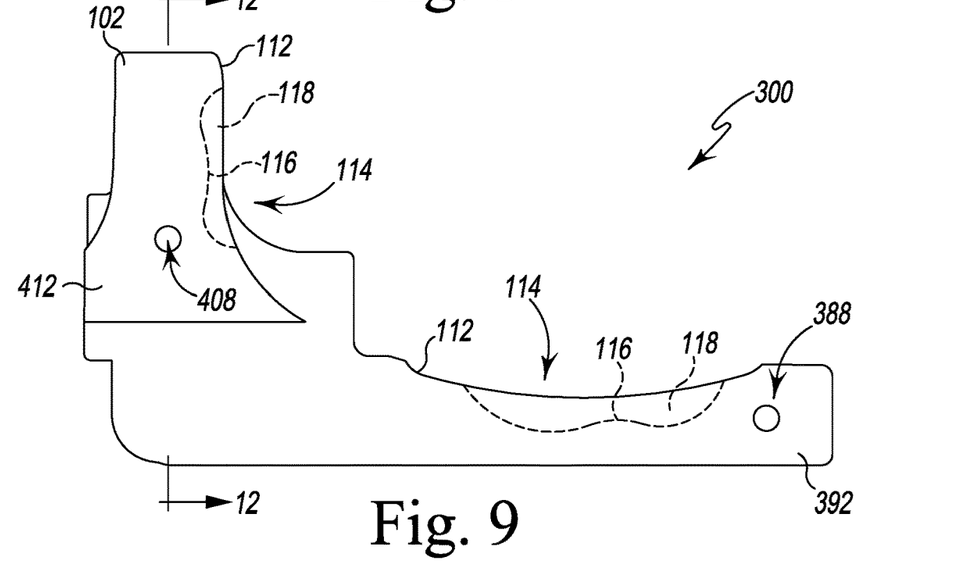
FIG. 9 is a top plan view of the surgical instrument of FIGS. 7-8.

As shown in FIGS. 9 and 11, the tab 104 includes a bore 388 that extends through a medial surface 390 and opposite lateral surface 392 of the tab. In the illustrative embodiment, the bore 388 passes through the passageway 380 and extends along an axis 394 extending perpendicular to the axis 382 of the passageway 380. The bore 388 is defined by a cylindrical wall 396 extending between the surfaces 390, 392. In the illustrative embodiment, the wall 366 is substantially devoid of metallic coating. It should be appreciated that in other embodiments the bore 356 may not extend through both the medial and lateral surfaces. It should also be appreciated that in some embodiments the bore may extend non-orthogonally to the passageway.

Figure 12:
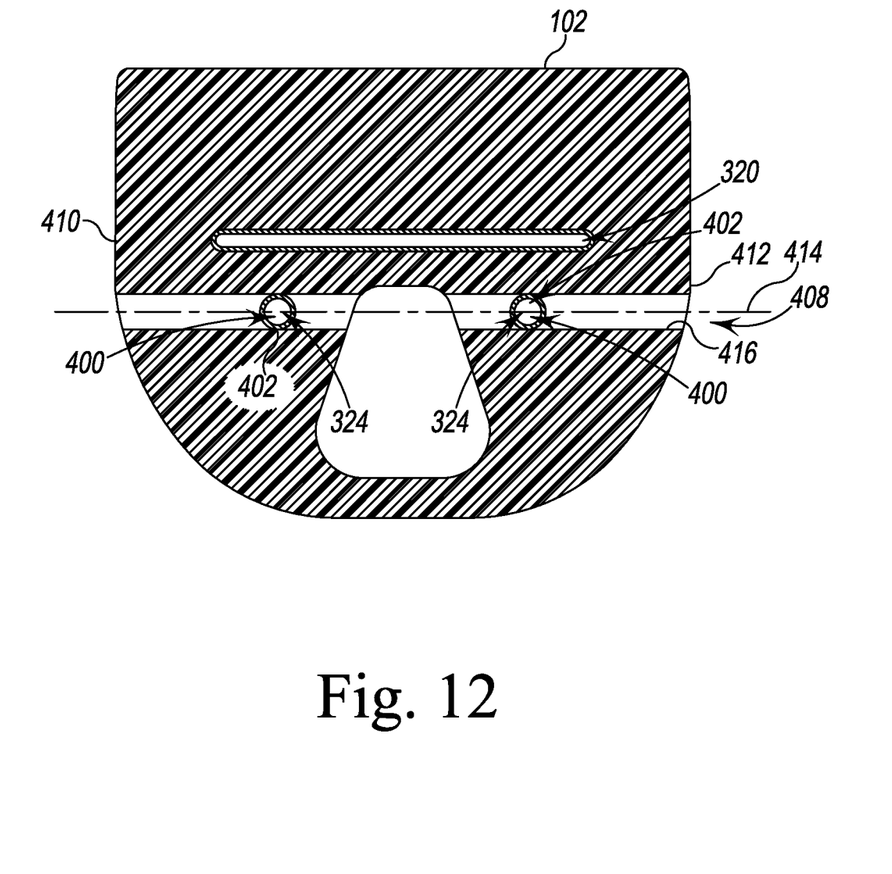
FIG. 12 is a cross-sectional elevation view taken along the line 12-12 in FIG. 9.

Referring now to FIG. 12, the configuration of each pin guide 324 largely mirrors that of the pin guides 330. Each pin guide 324 has a passageway 400 that extends through the anterior surface 342 and posterior surface 346 of the base 102. A metallic layer or coating 402 lines each passageway 400.

As shown in FIGS. 9 and 12, the base 102 includes a bore 408 that extends through a medial surface 410 and lateral surface 412 base 102. In the illustrative embodiment, the bore 408 passes through the passageways 400 and extends along an axis 414 (FIG. 12) extending perpendicular to the axes of the passageway 400. The bore 408 is defined by a cylindrical wall 416 extending between the surfaces 410, 412. In the illustrative embodiment, the wall 416 is substantially devoid of metallic coating. It should be appreciated that in other embodiments the bore 408 may not extend through both the medial and lateral surfaces. It should also be appreciated that in some embodiments the bore may extend non-orthogonally to the passageways.

During the manufacture of the cutting block 300, the bores 358, 388, and 408 provide pathways for the electrolyte solution containing metallic salts to advance into the passageways 320, 380, 400. In one illustrative method, the block 100 may be manufactured by forming its base as a single, monolithic component from a polymeric material. This single, monolithic component may then be immersed in an electrolyte solution containing metallic salts. The bores 358, 388, and 408 then provide pathways for the electrolyte solution containing metallic salts to advance into the passageways 320, 380, 400. The passageways 320, 380, 400 may then be exposed to one or electrodes within the solution to form the metallic layers thereon. It should be appreciated that in other embodiments other techniques may be used to form the metallic layers on the polymeric component. It should be appreciated that such bores may be incorporated into the cutting block 100 described above.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the method, apparatus, and system described herein. It will be noted that alternative embodiments of the method, apparatus, and system of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

The invention claimed is:

1. An orthopaedic surgical instrument comprising:
   a customized patient-specific instrument configured to be selectively attached at a predetermined location of a patient's bone, the customized patient-specific instrument comprising:
   a polymeric body including (i) a bone-facing surface having a customized patient-specific negative contour shaped to match and receive a corresponding positive contour of the patient's bone at the predetermined location, (ii) an outer surface positioned opposite the bone-facing surface, and (iii) an inner wall extending between a first opening defined in the bone-facing surface and a second opening defined in the outer surface, wherein the first opening is defined by a first edge and the second opening is defined by a second edge, and
   a metallic coating positioned on:
     (i) a first planar section of the inner wall extending inwardly from the first opening such that the metallic coating defines a first planar surface abutting the first edge of the first opening,
     (ii) a second planar section of the inner wall extending inwardly from the second opening such that the metallic coating defines a second planar surface abutting the second edge of the second opening,
     (iii) a third planar section of the inner wall extending inwardly from the first opening such that the metallic coating defines a third planar surface abutting the first edge of the first opening, and
     (iv) a fourth planar section of the inner wall extending inwardly from the second opening such that the metallic coating defines a fourth planar surface abutting the second edge of the second opening,
   wherein the first and third planar sections of the inner wall cooperate to define a first cutting slot having a first thickness sized to receive a cutting tool, wherein the second and fourth planar sections of the inner wall cooperate to define a second cutting slot having a second thickness sized to receive the cutting tool, wherein the inner wall includes a fifth section positioned between the first and second planar sections of the inner wall, wherein the inner wall includes a sixth section positioned between the third and fourth planar sections of the inner wall, and wherein the fifth and sixth sections of the inner wall cooperate to define a passageway having a third thickness greater than each of the first and second thicknesses such that the fifth and sixth sections are spaced apart from the cutting tool when the cutting tool is positioned in at least one of the first and second cutting slots.

2. The orthopaedic surgical instrument of claim 1, wherein the inner wall includes a first sloped surface extending between the first planar section and the fifth section and a second sloped surface extending between the second planar section and the fifth section.

3. The orthopaedic surgical instrument of claim 1, wherein the first thickness is equal to the second thickness.

4. The orthopaedic surgical instrument of claim 2, wherein the inner wall includes a third sloped surface extending between the third planar section and the sixth section and a fourth sloped surface extending between the fourth planar section and the sixth section.

* * * * *